(12) United States Patent
Silberberg et al.

(10) Patent No.: US 7,826,051 B2
(45) Date of Patent: Nov. 2, 2010

(54) COHERENTLY CONTROLLED NONLINEAR RAMAN SPECTROSCOPY

(75) Inventors: Yaron Silberberg, Lehavim (IL); Nirit Dudovich, Rehovot (IL); Dan Oron, Rehovot (IL)

(73) Assignee: Yeda Research and Development Company Ltd., Rehovot (IL)

( * ) Notice: Subject to any disclaimer, the term of this patent is extended or adjusted under 35 U.S.C. 154(b) by 266 days.

(21) Appl. No.: 11/597,190

(22) PCT Filed: May 27, 2004

(86) PCT No.: PCT/IL2004/000454

§ 371 (c)(1),
(2), (4) Date: Aug. 12, 2008

(87) PCT Pub. No.: WO2005/116596

PCT Pub. Date: Dec. 8, 2005

(65) Prior Publication Data

US 2008/0309931 A1    Dec. 18, 2008

(51) Int. Cl.
*G01J 3/44* (2006.01)
(52) U.S. Cl. .................................... 356/301
(58) Field of Classification Search ............. 356/301, 356/451, 453, 456; 372/25, 109
See application file for complete search history.

(56) References Cited

U.S. PATENT DOCUMENTS

| | | | |
|---|---|---|---|
| 3,782,828 A | 1/1974 | Alfano et al. | |
| 4,077,719 A | 3/1978 | Barrett et al. | |
| 4,084,100 A | 4/1978 | Begley et al. | |
| 4,277,760 A | 7/1981 | Eckbreth | |
| 4,405,237 A | 9/1983 | Manuccia et al. | |
| 4,512,660 A | 4/1985 | Goldberg | |
| 4,619,528 A | 10/1986 | Genack et al. | |
| 5,095,487 A | 3/1992 | Meyerhofer et al. | |
| 5,303,710 A | 4/1994 | Bashkansky et al. | |
| 5,689,362 A | 11/1997 | Kadota | |

(Continued)

FOREIGN PATENT DOCUMENTS

WO    02/06778 A1    1/2002

(Continued)

OTHER PUBLICATIONS

Zumbusch, A. et al., "Three-Dimensional Vibrational Imaging by Coherent Anti-Stokes Raman Scattering," *Physical Review Letters*, vol. 82, No. 20 pp. 4142-4145, (1999).

(Continued)

*Primary Examiner*—Tarifur Chowdhury
*Assistant Examiner*—Jonathan M Hansen
(74) *Attorney, Agent, or Firm*—The Nath Law Group; Derek Richmond

(57) ABSTRACT

A method and system (10) are presented for producing exciting radiation (P') to be used in producing an output coherent anti-stokes Raman scattering (CARS) signal of a medium (12). An input spectral phase coherent optical pulse (P), carrying a pump, a Stokes and a probe photon, is optically processed by adjusting spectral phase and polarization of wavelength components of the input pulse to produce a unitary optical exciting pulse (P') that carries the pump photon, the Stokes photon and multiple probe photons and is capable of inducing interference between contributions from at least some of vibrational levels in the CARS signal.

39 Claims, 4 Drawing Sheets

U.S. PATENT DOCUMENTS

| | | | |
|---|---|---|---|
| 6,108,081 | A | 8/2000 | Holtom et al. |
| 6,175,437 | B1 | 1/2001 | Diels et al. |
| 6,327,068 | B1 | 12/2001 | Silberberg et al. |
| 7,092,086 | B2 | 8/2006 | Knebel |
| 7,106,436 | B1 | 9/2006 | Gord et al. |
| 7,256,885 | B2 * | 8/2007 | Silberberg et al. .......... 356/301 |
| 7,403,282 | B2 * | 7/2008 | Silberberg et al. .......... 356/301 |
| 2002/0172243 | A1 | 11/2002 | Ono et al. |
| 2003/0099264 | A1 | 5/2003 | Dantus et al. |
| 2003/0160955 | A1 | 8/2003 | Xie et al. |
| 2004/0065845 | A1 | 4/2004 | Seyfried |
| 2004/0113059 | A1 | 6/2004 | Kawano et al. |
| 2004/0145735 | A1 | 7/2004 | Silberberg et al. |

FOREIGN PATENT DOCUMENTS

WO        02/48660 A1    6/2002

OTHER PUBLICATIONS

Potma, E.O., et al., "Real-time visualization of intracellular hydrodynamics in single living cells," *Proc. Natl. Acad. Sci.* vol. 98, No. 4, pp. 1577-1582, (2001).

Müller, M., et al., "CARS microscopy with folded BoxCARS phasematching," *Journal of Microscopy*, vol. 197, pp. 150-158, (2000).

Warren, W.S., "Robust approaches to laser selective chemistry and quantum molecular control," *Proc. SPIE*, vol. 2124, pp. 78-83, (1994).

Schrader, B., "Infrared and Raman Spectroscopy," *VCH Weinheim*, pp. 172-183, (1995).

Oron, D., et al., "Femtosecond Phase-and-Polarization Control for Background-Free Coherent Anti-Stokes Raman Spectroscopy," *Physical Review Letters*, vol. 90, No. 21, pp. 213902-1-213902-4, (2003).

Weiner, A.M., "Femtosecond pulse shaping using spatial light modulators," *Review of Scientific Instruments*, vol. 71, No. 5, pp. 1929-1960, (2000).

Oron, D., et al., "Narrow-Band Coherent Anti-Stokes Raman Signals from Broad-Band Pulses," *Physical Review Letters*, vol. 88, No. 6, pp. 063004-1-063004-4, (2002).

Brixner, T., et al., "Femtosecond Polarization pulse shaping," *Optics Letters*, vol. 26, No. 8, pp. 557-559, (2001).

Brixner, T., et al., "Generation and characterization of polarization-shaped femtosecond laser pulses," *Appl. Phys. B.* vol. 74, (Suppl.), pp. S133-S144, (2002).

Dudovich, N., et al., "Single-pulse coherently controlled nonlinear Raman Spectroscopy and microscopy," *Nature*, vol. 418, pp. 512-514, (2002).

Judson, R.S., "Teaching Lasers to Control Molecules," *Physical Review Letters*, vol. 68, No. 10, pp. 1500-1503, (1992).

Scully, M.O., et al., "FAST CARS: Engineering a laser spectroscopic technique for rapid identification of bacterial spores," *Proc. Natl. Acad. Sci.*, vol. 99, No. 17, pp. 10994-11001, (2002).

Gniadecka, M., et al., "Diagnosis of Basal Cell Carcinoma by Raman Spectroscopy," *Journal of Raman Spectroscopy*, vol. 28, pp. 125-129, (1997).

Leonhardt, R., et al., "Terahertz Quantum Beats in Molecular Liquids," *Chemical Physics Letters*, vol. 133, No. 5, pp. 373-377, (1987).

Hashimoto, M, et al., "Molecular vibration imaging in the fingerprint region by use of coherent anti-Stokes Raman scattering microscopy with a collinear configuration" *Optics Letters*, vol. 25, No. 24, pp. 1768-1770, (2000).

Volkmer, A., et al., "Time-resolved coherent anti-Stokes Raman scattering microscopy: Imaging based on Raman free induction decay," *Applied Physics Letters*, vol. 80, No. 9, pp. 1505-1507, (2002).

Oron, D., et al., "Quantum control of coherent anti-Stokes Raman processes," *Physical Review A*, vol. 65, pp. 043408-1-043408-4.

XP-002285596: Oron, D., et al., Single-Pulse Phase-Contrast Nonlinear Raman Spectroscopy, *Physical Review Letters*, vol. 89, No. 27, pp. 27300-1-27300-4, (2002).

Jonas, D.M., "Two-Dimensional Femtosecond Spectroscopy," *Annu. Rev. Phys. Chem.*, vol. 54, pp. 425-463, (2003).

Dudovich, N., et al., "Single-pluse coherent anti-Stokes Raman spectroscopy in the fingerprint spectral region," *Journal of Chemical Physics*, vol. 118, No. 20, pp. 9208-9215, (2003).

XP-002285597: Silberberg, Y., et al., "New methods in femtosecond multiphoton microscopy," *Proc.SPIE: Microphoton Microscopy in the Biomedical Sciences III*, vol. 4963, No. 1, pp. 209-222, (2003).

XP-002219151: Oudar, J-L., et al., "Polarization-sensitive coherent anti-Stokes Raman spectroscopy," *Applied Physical Letters, American Institute of Physics*, vol. 34, No. 11, pp. 758-760, (1979).

XP-001124324: Cheng, J-X et al. "Polarization Coherent anti-Stokes Raman scattering microscope," *Optics Letters*, vol. 26, No. 17, pp. 1341-1343, (2001).

XP-002285598: Meshulach, D., et al., "Coherent quantum control of two-photon transitions by a femtosecond laser pulse," *Nature*, vol. 396, pp. 239-242, (1998).

XP-002285599: Meshulach, D., et al., "Coherent quantum control of multiphoton transitions by shaped ultrashort optical pulses," *Physical Review A*, vol. 60, No. 2, pp. 1287-1292, (1999).

\* cited by examiner (General art)

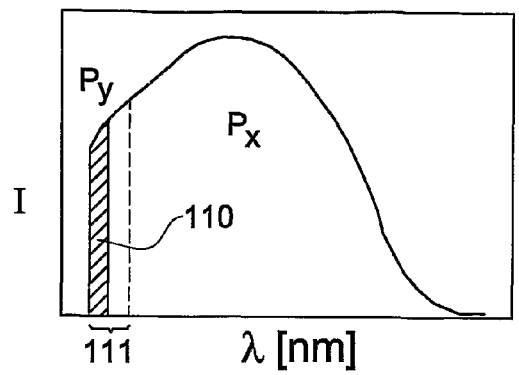
FIG. 5A
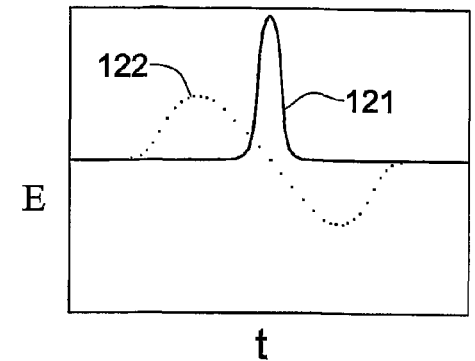
FIG. 5B
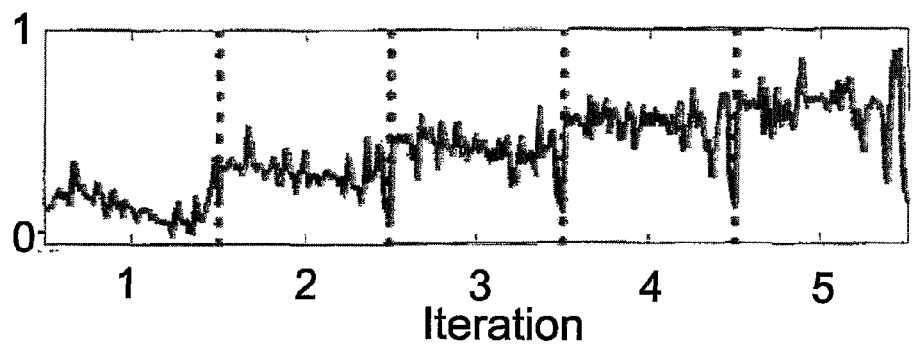
FIG. 6A
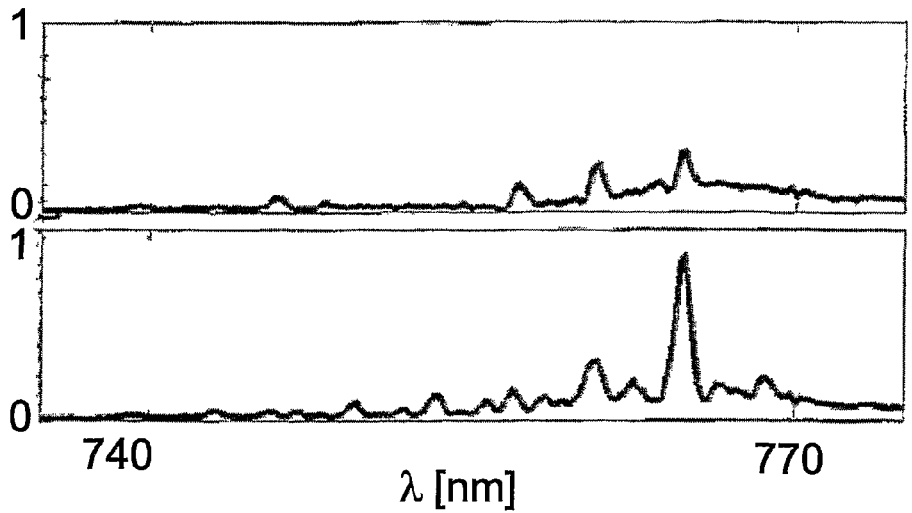
FIG. 6B
FIG. 6C

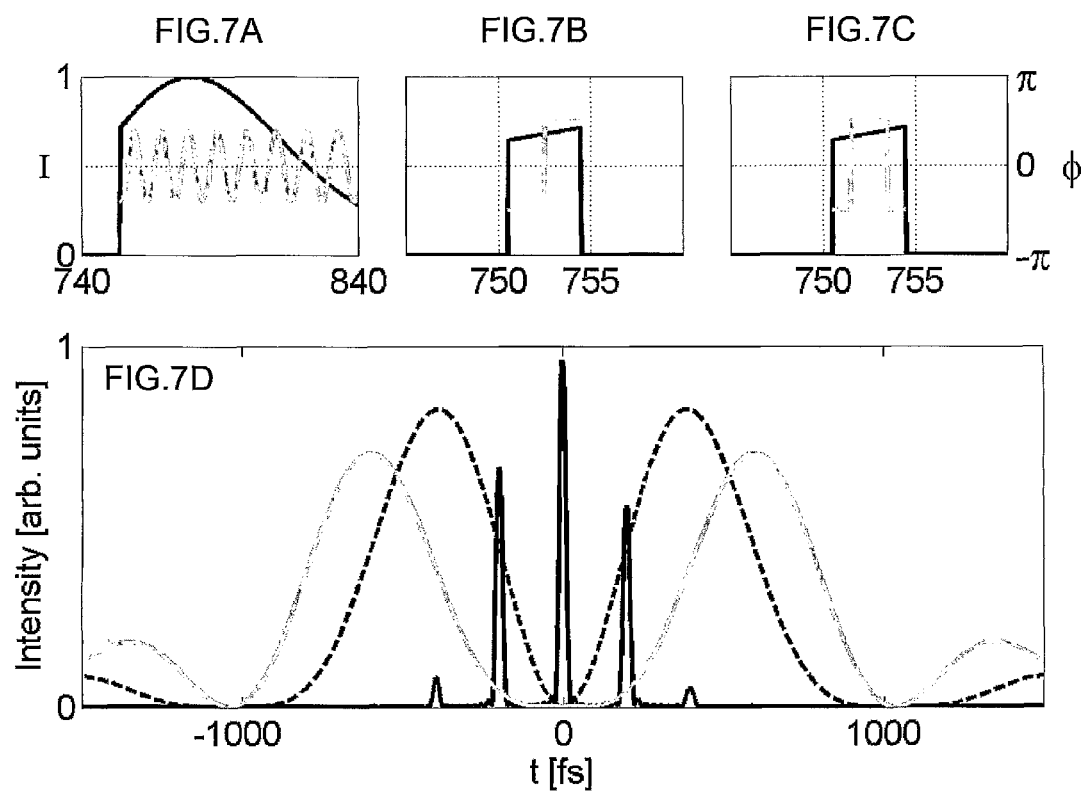

COHERENTLY CONTROLLED NONLINEAR RAMAN SPECTROSCOPY

CROSS-REFERENCE

This is a National Phase Application filed under 35 U.S.C. §371 as a national stage of PCT/IL2004/000454, filed on May 27, 2004, the entire content of which is hereby incorporated by reference.

FIELD OF THE INVENTION

This invention relates to relates to Raman spectroscopy, and in particular, to coherent anti-stokes Raman spectroscopy.

LIST OF REFERENCES

The following references are considered to be pertinent for the purpose of understanding the background of the present invention:

1. A. Zumbusch, G. R. Holtom, X. S. Xie, Phys. Rev. Lett. 82, 4142 (1999);
2. E. O. Potma, W. P. de Boeij, P. J. M. van Haastert, D. A. Wiersma, Proc. Natl. Acad. Sci. 98, 1577 (2001);
3. M. Muller, J. Squier, C. A. de Lange, G. J. Brakenhoff, J. Microscopy 197, 150 (2000);
4. W. S. Warren, Proc. SPIE 2124, 78 (1994);
5. *Infrared and Raman Spectroscopy*, edited by B. Schrader (VCH, Weinheim, 1995);
6. D. Oron, N. Dudovich, Y. Silberberg, Phys. Rev. Lett. 90, 213902 (2003);
7. "*Narrow-Band Coherent Anti-Stokes Raman Signals from Broad-Band Pulses*", D. Oron, N. Dudovich, D. Yelin, Y. Silberberg, Phys. Rev. Lett. 88, 063004 (2002);
8. A. M. Weiner, Rev. Sci. Inst. 71, 1929 (2000);
9. T. Brixner, G. Gerber, Opt. Lett. 26, 557 (2001); T. Brixner, G. Krampert, P. Niklaus, G. Gerber, Appl. Phys. B 74, S133 (2002);
10. N. Dudovich, D. Oron, Y. Silberberg, Nature 418, 512 (2002);
11. S. R. Judson, H. Rabitz, Phys. Rev. Lett. 68, 1500 (1992);
12. N. Dudovich, D. Oron, Y. Silberberg, J. Chem. Phys. 118, 9208 (2003);
13. M. O. Scully et al., Proc. Natl. Acad. Sci. 99, 10994 (2002);
14. M. Gnaideka, H. C. Wulf, N. N. Mortensen, O. F. Nielsen, D. H. Christensen, J. Raman Spec. 28, 125 (1997);
15. Leonhardt et al., published in Chem. Phys. Lett., 1987, V. 133, P. 373;
16. U.S. Pat. No. 4,077,719;
17. U.S. Pat. No. 4,084,100;
18. U.S. Pat. No. 4,405,237;
19. U.S. Pat. No. 4,512,660;
20. WO 02/48660;
21. U.S. Pat. No. 6,108,081;
22. WO 02/06778;
23. Zumbusch et al., Phys. Rev. Lett., 1999, V. 82, P. 4142;
24. Hashimoto et al., Opt. Lett., 2000, V. 25, P. 1768;
25. Volkmer at al., Applied Phys. Lett., 2002, V. 80, P. 1505;
26. U.S. Pat. No. 6,327,068;
27. "*Quantum Control of Coherent anti-Stokes Raman Processes*", by Oron et al., Phys. Rev. A, 2002, V. 65, P. 043408;
28. "*Single-Pulse Phase-Contrast Nonlinear Raman Spectroscopy*", Oron et al., Phys. Rev. Let., Vol. 89, N. 27, 273001-1-273001-4, 2002.
29. "*Two-dimensional femtosecond spectroscopy*", D. M. Jonas, Annu. Rev. Phys. Chem., Vol. 54, 425-463, 2003.

BACKGROUND OF THE INVENTION

Optical spectroscopy typically requires post-processing of a measured spectrum, where, by correlation with known tabulated spectra the various measured lines are attributed to known substances. In incoherent spectroscopy, this is the only way to differentiate between contributions of various substances. This often requires detailed knowledge of lineshapes and relative intensities and in many cases requires more experimental data.

Coherent Raman processes have recently attracted considerable interest, in particular due to their potential for chemically sensitive microscopy of untreated biological specimen [1-3]. Generally, in coherent nonlinear spectroscopy, a sample is probed by measuring processes of energy exchange between photons interacting with the sample. One of the most common nonlinear spectroscopy methods is coherent anti-stokes Raman scattering (CARS), a coherent four-wave mixing process involving the generation of a coherent vibration in the probed medium. In CARS, three photons, a pump photon ($\omega_p$) a probe photon ($\omega_{pr}$) and the Stokes photon ($\omega_s$), overlap in the medium under investigation. By nonlinear interaction with the molecules a fourth coherent photon ($\omega_{AS}$) with the anti-Stokes frequency $\omega_{AS}=\omega_p-\omega_s+\omega_{pr}$ is generated.

The CARS process can be visualized in a molecular energy level diagram as depicted in FIG. 1, where |i> and |g> are molecular rovibrational states, and |α> and | are virtual levels. Resonant enhancement of the CARS process occurs when the frequency difference $\Omega_R=\omega_p-\omega_s$ coincides with a vibrational level of the medium.

The CARS process, as a coherent scattering process, has to fulfill a phase matching condition, which is equivalent to momentum conservation of the photons involved. With the wave vectors of the pump photon ($k_P$), the probe photon ($k_{pr}$) and the Stokes photon ($k_S$), the wave vector of the Raman signal can be obtained by $$k_{AS}=k_{pr}+(k_P-k_S) \text{ or } k_P+k_{pr}=k_S+k_S.$$

In general, there are two conventional different techniques utilizing a multi-beam excitation scheme for measuring a CARS spectrum, as disclosed, for example, in [16]-[20]. According to the first technique, the so-called scanning CARS, two narrow bandwidth lasers at $\omega_p$ and at $\omega_s$ (having spectral width of the order of the typical linewidth of Raman levels, i.e., 1 cm$^{-1}$) are tuned over the Raman resonances of the probed species to generate a signal at $2\omega_p-\omega_s$ (in this case $\omega_{pr}=\omega_s$). The spectral resolution of this technique is mainly determined by the bandwidth of the applied laser sources. According to the second technique, broadband or multiplex CARS, a broadband Stokes beam (spectral width typical 100-1000 cm$^{-1}$) can be used to excite several Raman transitions under investigation simultaneously. The use of a narrow band probe and a broadband Stokes beam enables simultaneous measurement of the entire band of the Raman spectrum [5]. The spectral resolution of this technique is usually achieved by using a monochromator and a multichannel detection system. Thus, one laser shot is utilized to measure an entire band of molecular vibrations.

Another possibility to obtain CARS spectra is to use a time-resolved CARS scheme. In this technique, two relatively broadband exciting pulses are used for simultaneously populating several Raman levels. The spectral data is obtained by measuring the beating pattern of the CARS signal from a third, delayed broadband probe pulse, as a function of the probe delay [15].

Coherent Raman processes have become a valuable tool in the past few decades in femtosecond time-resolved spectroscopy, as well as in combustion studies and condensed-state spectroscopy. For example, according to [15], the measurements of the energy difference and the lifetimes of two (or more) Raman levels by Fourier-decomposing the quantum beats of the CARS signal are measured using femtosecond pulses. This scheme has been recently used to analyze the energy-level diagram of complex molecules.

CARS has recently become a favorable technique for nonlinear depth-resolved microscopy [21]-[25]. CARS microscopy has the potential, for example, for studying live biological specimens while gathering three-dimensional information on their molecular constitution. However, these CARS microscopes also require two or three narrow-band sources that must be all tightly synchronized and also tunable within the Raman energy range.

It should be appreciated that the signal of CARS (being a result of a nonlinear process) is stronger with short intense pulses. However, the femtosecond CARS techniques suffer from two major difficulties. First, there is an increased strong background, typically due to the electronic contributions to the third-order susceptibility, both from the sample and from the surrounding medium (i.e., solvent). The second difficulty is associated with a lack of selectivity between neighboring energy levels, due to the large bandwidth of the pulses.

These problems can be solved by coherent quantum control methods. The concept of coherent quantum control of a quantum system is based on the achievement of constructive interference between different quantum paths leading to a desirable outcome, while interfering destructively with paths leading to other outcomes. While schemes of coherent control may involve excitations by continuous waves, most available techniques are also known which involve ultrashort optical pulses. With the recent progress in ultrafast optics, it is now possible to shape ultrashort signals with desired spectral shapes ([6] assigned to the assignee of the present application).

The inventors of the present invention have recently shown how coherent control techniques can be exploited to improve the CARS spectroscopy employing three femtosecond pulses related to the pump, Stokes and probe beams, respectively. Two approaches have been described for controlling the CARS process. According to the first approach [27], a periodic phase modulation is used to control the population induced by broadband pulses. By shaping both the pump and the Stokes pulses with an appropriate spectral phase function, the nonresonant CARS background has been greatly reduced. This technique also allows for exciting just one out of many vibrational levels, even when all of them are within the spectral bandwidth of the excitation pulses. According to the second approach [7], only the probe pulse is shaped, thereby enabling enhancement of the resolution of the measured CARS spectrum. The achieved spectral resolution becomes significantly better than the bandwidth of the readout pulse. In particular, by tailoring the phase of a 100 femtosecond probe pulse, a narrow-band CARS spectroscopy resonant signal has been obtained with a width of less than $15 \text{ cm}^{-1}$, which is an order of magnitude narrower than the CARS signal from an unshaped, transform limited pulse (all frequency components having the same phase).

SUMMARY OF THE INVENTION

There is a need in the art to facilitate coherent anti-stokes Raman scattering (CARS) spectroscopy by providing a novel method and system for producing an exciting signal to induce a CARS process in a medium.

The main idea of the present invention is associated with the following: In spectroscopy, the fingerprint of a substance is usually comprised of a sequence of spectral lines with characteristic frequencies and strengths. Identification of substances often involves post-processing, where the measured spectrum is compared with tabulated fingerprint spectra. Even with coherent Raman processes, despite the coherent nature of these processes, the common wisdom of analysis of the measured spectra remained correlation with known tabulated spectra, not making any use of the coherence properties of the signal. The present invention utilizes this coherence, taking advantage of the ability to induce interference between contributions originating from several vibrational levels. Rather than considering a single vibrational level at a time, a number of levels is practically grouped into a single entity, which serves as a much better spectroscopic fingerprint.

The technique of the present invention takes advantage of the previous technique, recently developed by the inventors of the present invention. This recent development has demonstrated the possibility of single-pulse CARS spectroscopy, where the pump, the Stokes and the probe photon are supplied by the same laser pulse [10,12, 28, 29]. Three approaches to both retaining the spectral selectivity and overcoming the strong nonresonant background accompanying CARS driven impulsively by an ultrashort pulse were demonstrated. According to the first approach, a periodic phase modulation was applied to the input laser pulse, resulting in selective excitation of only a part of the Raman levels with energies within the spectral bandwidth of the laser pulse [10, 12]. According to the second approach, the input pulse was effectively split into a broadband pump and a narrow-band probe differentiated by their relative phase. In this approach, spectral information is obtained by monitoring the interference pattern between the nonresonant background and the resonant CARS signal in the measured CARS spectrum [12,28]. According to the third approach, input pulse was effectively split into a broadband pump and a narrow-band probe differentiated by both their polarization and their timing. Since there is no temporal overlap between the pump and probe components, this results in complete rejection of the instantaneous nonresonant background. The Raman spectrum is thus reflected as isolated spectral peaks in the anti-Stokes part of the spectrum.

The present invention provides for significant reduction in the necessary post-processing, simplified detection (since measurement of the entire CARS spectrum is unnecessary), an increase in the induced CARS signal and better rejection of both resonant and nonresonant coherent background by providing a nonlinear spectroscopy method and system, where, through coherent control of the nonlinear process, the information from the entire spectrum can be practically collected into a single coherent entity. This is implemented by inducing a CARS process in a medium by a single pulse carrying a pump photon, a Stokes photon and multiple probe photon, wherein the phase and polarization of this pulse is adjusted so as to cause interference between contributions to the total signal originating from several (at least two) Raman levels induced by said pulse.

The so obtained pulse with the appropriately adjusted phase and polarization will be referred to herein as "unitary optical excitation pulse" enabling identification of a CARS signal induced by this pulse from any other optical signal. This unitary optical excitation pulse is produced by tailoring a transform limited pulse generated by a laser source and carrying a pump photon, a Stokes photon and a probe photon. The term "transform limited pulse" used herein actually signifies a pulse resulted from phasing the modes of a compressible phase coherent pulse, and can therefore be termed also as a "spectral phase coherent pulse" or "compressible to a transform limited pulse". The technique of the present invention results in that a "processed" CARS spectrum becomes concentrated in a single spectral component, and therefore it is possible to use a simple filter for processing a signal coming from the medium (rather than a spectrometer).

There is thus provided according to one broad aspect of the present invention, a method for producing exciting radiation to be used in producing an output coherent anti-stokes Raman scattering (CARS) signal of a medium, the method comprising: tailoring an input coherent optical pulse carrying a pump photon, a Stokes photon and a probe photon, said tailoring comprising adjusting spectral phase and polarization of wavelength components of the spectral phase coherent optical pulse to produce a unitary optical exciting pulse that carries the pump photon, the Stokes photon and multiple probe photons and is capable of inducing a CARS signal, which results from an interference between contributions from at least two vibrational levels.

The pulse tailoring (shaping) is also determined by whether the interference is to be constructive, or be destructive for at least some of the vibrational levels.

The method of the present invention thus enables all-optical processing of the entire vibrational spectrum. This results in a significant reduction in the required post-processing of the measured signal. Moreover, it allows coherent subtraction of resonant background lines unattainable by any other means. This is because the tailoring results in that a CARS spectrum is concentrated in a single spectral component, thereby allowing for using a simple filter to extract the CARS signal, rather than using a spectrometer. Preferably, the tailoring of the input pulse includes blocking wavelengths shorter than a predetermined wavelength in the pulse. This predetermined wavelength is defined by a spectral bandwidth in which the output CARS signal is likely to occur.

The tailoring of the input pulse includes three parts: assigning a desired polarization to each spectral component of the pulse (e.g., by shifting the phase of the probe photon) in order to provide orthogonal polarizations for probe and pump photons; assigning a desired phase to each of the polarization shifted (probe) components, comprising both an internal phase structure and an overall phase; assigning a desired phase to the unshifted (pump) spectral components. The desired phases and polarizations are assigned by modulating the spectral phase of the spectral phase coherent optical pulse on two orthogonal polarization axes.

Preferably, the spectral location of the polarization shifted (probe) components is determined by the Raman level structure of the probed medium, so as to induce interference of contributions from different Raman levels in the CARS spectrum. The amount of polarization rotation is determined by the relative strength of the Raman levels to be measured, in order to generate a predetermined interference pattern between them.

Preferably, the internal phase structure of each polarization shifted (probe) component consists of one or more π-phase gates of a varying spectral bandwidth. This is determined by the need to minimize the temporal overlap between the pump and the probe components for optimal background rejection. The overall phase of each polarization-shifted component is determined according to the required, predetermined interference pattern between the various Raman levels, i.e. constructive or destructive interference.

Preferably, the spectral phase function of the pump component is a flat phase, a linear phase (corresponding to a temporal delay), or a periodic function. The use of a periodic function enables to perform single-pulse two-dimensional Raman spectroscopy [29] using phase-and-polarization coherent control aimed at measuring anharmonicity or the coupling between two excited states and thus providing more structural information about the probed medium. According to this technique, one of the two time scales is introduced by applying a periodic phase modulation of the x-polarized component of the excitation pulse (e.g., using a sinusoidal function). This time scale is controlled by changing the modulation frequency of the spectral phase function. The second time scale is introduced by spectrally dispersing the signal from a shaped, narrow-bandy-polarized probe.

According to another aspect of the invention, there is provided a method for producing exciting radiation to be used in producing an output coherent anti-stokes Raman scattering (CARS) signal of a medium, the method comprising: tailoring an input spectral phase coherent optical pulse carrying a pump photon, a Stokes photon and a probe photon, said tailoring comprising adjusting spectral phase and polarization of wavelength components of the spectral phase coherent optical pulse to produce a unitary optical exciting pulse that carries the pump photon, the Stokes photon and multiple probe photons and is capable of inducing a CARS signal, which results from an interference between contributions from at least two vibrational levels, a CARS spectrum therefore being concentrated in a single spectral component, thereby significantly simplifying filtering of a signal coming from the medium to extract the CARS signal therefrom.

According to yet another broad aspect of the invention, there is provided a method for producing an output coherent anti-stokes Raman scattering (CARS) signal of a medium, the method comprising:

(a) generating an input spectral phase coherent optical pulse carrying a pump photon, a Stokes photon and a probe photon;

(b) tailoring spectral properties of the input pulse, said tailoring comprising adjusting spectral phase and polarization of wavelength components of the input pulse to produce a unitary optical exciting pulse that carries the pump photon, the Stokes photon and multiple probe photons and is capable of inducing interference between contributions from vibrational levels in the CARS signal excited in the medium by said exciting pulse, said multiple probe photons having the same polarization which is orthogonal to that of the pump photons;

(c) passing radiation coming from the medium through a polarizer to thereby separate the excited CARS signal from a background.

According to yet another aspect of the invention, there is provided a system for use in measuring an output coherent anti-stokes Raman scattering (CARS) signal of a medium, the system comprising a pulse shaper assembly configured and operable to apply tailoring to an input coherent optical pulse, said tailoring comprising adjusting spectral phase and polarization of wavelength components of the spectral phase coherent optical pulse to produce an exciting pulse that carries desired wavelength components and is capable of, when interacting with the medium, inducing interference between contributions from several vibrational levels in the CARS signal excited in the medium.

According to yet another aspect of the invention, there is provided a system for use in measuring an output coherent anti-stokes Raman scattering (CARS) signal of a medium, the system comprising:

a pulse shaper assembly configured and operable to apply tailoring to an input coherent optical pulse, said tailoring comprising adjusting spectral phase and polarization of wavelength components of the spectral phase coherent optical pulse to produce an exciting pulse that carries desired wavelength components and is capable of, when interacting with the medium, inducing interference between contributions from several vibrational levels in the CARS signal excited in the medium, a spectrum of the CARS signal being therefore concentrated to a single spectral component;

a filter assembly for accommodating in a path of radiation coming from the medium, the filter assembly comprising a polarizer, and a spectral filter configured for separating the single spectral component from the radiation coming from the medium.

According to yet another aspect of the present invention, there is provided a system for use in measuring an output coherent anti-stokes Raman scattering (CARS) signal of a medium, the system comprising:

a single laser operable to generate at least one input spectral phase coherent optical pulse carrying a pump photon, a Stokes photon and a probe photon; and a pulse shaper assembly configured and operable to tailor the input pulse, said tailoring comprising adjusting spectral phase and polarization of wavelength components of the input pulse to produce an exciting pulse that carries desired wavelength components including the pump, Stokes and multiple probe photons and is capable of, when interacting with the medium, inducing interference between contributions from several vibrational levels in the CARS signal excited in the medium;

a polarizer assembly for accommodating in an optical path of radiation coming from the medium to filter this radiation to extract the CARS signal from a background radiation.

The pulse shaper assembly includes an input dispersive element for spatially separating between the wavelength components in the input pulse; a Spatial Light Modulator (SLM) operable to apply spectral phase shaping and polarization rotation to selected components from said wavelength components; and an output dispersive element for recombining at least some of the wavelength components into the output exciting pulse. The pulse shaper preferably also includes a spectral filter operable to block a desired wavelength range in the input pulse (that of the expected CARS signal) to prevent radiation of this wavelength range from reaching the medium. The SLM is operable to apply to radiation passing therethrough a suitable spectral phase function so as to provide the exciting pulse carrying the pump photon, the Stokes photon and multiple probe photons, such that the probe photons include those defined by the expected Raman levels, selected so as to cause interference between photons scattered off different Raman levels. Additionally, the SLM operates to provide orthogonal polarizations for the pump and probe photons. Preferably, the SLM is a dual cell SLM type.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 3A and 3B graphically illustrate the multiple-probe CARS process according to the invention, wherein FIG. 3A is a schematic description of the excitation pulse, and FIG. 3B is a schematic description of the interference in the CARS spectrum;

FIGS. 4A to 4C exemplify CARS spectra from 1,2-dichloroethane obtained with the technique of the present invention, wherein FIG. 4A shows CARS spectrum using a single probe band (at 782 nm), FIG. 4B shows a CARS spectrum using a pulse with three probe bands (at 782 nm, 804 nm, 811 nm, all in phase and fully y-polarized) designed to induce constructive interference between the contributions of the three levels to the peak at 764 nm, and FIG. 4C shows CARS spectrum using a pulse with three probe bands designed to induce destructive interference at 764 nm between the contributions of the three levels.

FIGS. 5A and 5B exemplify the spectral phase shaping effect in the case of a spectral phase function in the form of a single $\pi$ phase-shifted gate introduced at a y-polarization shifted band, serving as a probe, wherein FIG. 5A shows the spectral intensity of a phase and polarization shaped exciting pulse, and FIG. 5B shows the electric field envelope versus time for phase and polarization shaped pulses; and FIGS. 6A to 6C exemplify an adaptive optimization of the signal at 765 nm from 1,2-dichloropropane, wherein FIG. 6A shows the signal at 765 nm during the five iterations of the optimization procedure, FIG. 6B shows the measured CARS spectrum at the end of the first iteration, and FIG. 6C shows the measured CARS spectrum at the end of the fifth iteration.

FIGS. 7A to 7C show schematically an example for possible pulse shapes to be used in single-pulse multidimensional Raman spectroscopy, wherein FIG. 7A shows the x-polarized pump intensity and phase, FIGS. 7B and 7C show two possible choices for the y-polarized probe intensity and phase, and FIG. 7D shows how the probe-free time window, necessary to achieve good rejection of the nonresonant background, is increased in going from the pulse shape of FIG. 7B to that of FIG. 7C, enabling nearly no temporal overlap with the pump depicted in FIG. 7A.

DETAILED DESCRIPTION OF THE INVENTION

Figure 1:
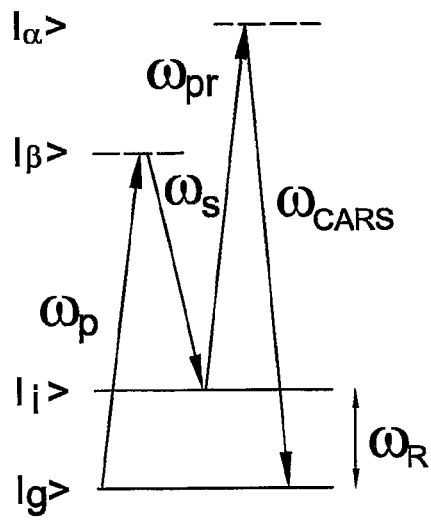
FIG. 1 is an energy level diagram of the typical CARS process.

FIG. 1 schematically illustrates a molecular energy level diagram showing the general principles of the CARS process, where |i> and |g> are molecular rovibrational states, and |α> and |β> are virtual levels. Resonant enhancement of the CARS process occurs when the frequency difference $\Omega_R = \omega_p - \omega_s$ coincides with a vibrational level of the medium.

The technique of the present invention provides a novel spectroscopic method applicable for coherent nonlinear spectroscopy, which eliminates or at least significantly reduces the need for post-processing of the measured spectra, typical of optical spectroscopy. To this end, the present invention utilizes an exciting pulse designed to induce interference between contributions from several vibrational levels, thus facilitating all-optical processing of the entire vibrational spectrum. This is implemented by grouping a number (at least two) of levels, which serve as a much better spectroscopic fingerprint, into a single entity, rather than considering a single energy level at a time. More specifically, these energy levels are simultaneously excited using a broadband pulse in which the probe pulse polarization and phase are tailored to direct the interference between contributions to the CARS signal arising from the energy levels to a single signal frequency. Thus, the CARS spectrum is concentrated in a single spectral component, and therefore provides for simple filtering of a signal coming from the medium, rather than using a spectrometer. The tailoring of the input signal is achieved by using phase-and-polarization coherent control, either in an open-loop or in an adaptive manner, of single-pulse coherent anti-Stokes Raman spectroscopy (CARS). The phase and polarization control is aimed at producing a broadband excitation pulse and a multiple frequency probe which, when combined, carry pump, Stokes and probe photons, wherein the probe photons are selected to include probe photons corresponding to Raman levels to be excited in the medium and to induce interference (destructive or constructive) between the contributions to the CARS signal from several excited Raman levels, and wherein all the probe photons have polarization orthogonal to that of the pump photons.

Figure 2:
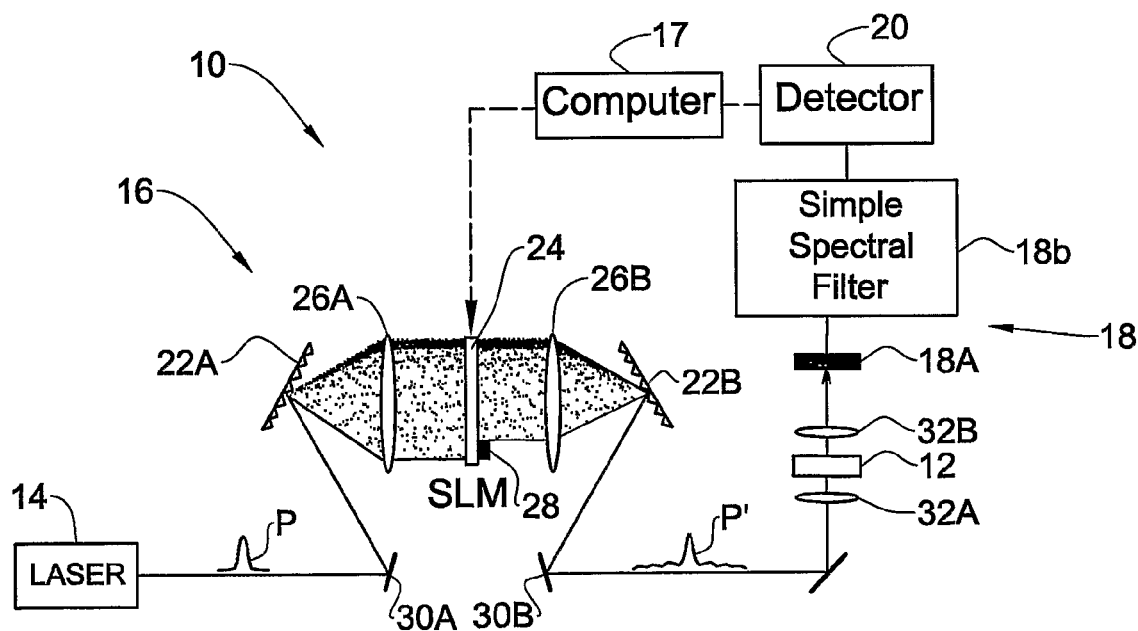
FIG. 2 schematically illustrates a CARS system according to the invention.

Referring to FIG. 2, there is schematically illustrated a CARS measurement system (spectrometer) 10 of the present invention associated with a sample holder 12 containing a medium under investigation. The system 10 includes a single laser 14 for generating an input pulse P; a pulse controlling assembly 16 operated by a control unit 17 to process the pulse P to produce a desired exciting pulse P'; a filtering assembly 18 for filtering a signal coming from the medium to separate a CARS signal (single spectral component) from a background signal; and a detector unit 20 for collecting the filtered CARS signal and generating data indicative thereof. Also provided in the system is an appropriate light directing optics for directing the input pulse to the pulse controlling assembly, directing the tailored pulse to the medium, and directing the CARS signal to the detector.

The laser 14 is adapted for producing optical transform-limited (spectral phase coherent) driving pulses P wherein each such pulse carries a pump photon, a Stokes photon and a probe photon which are necessary for exciting the medium and inducing the CARS process therein. This may be any laser capable of generating spectral phase coherent pulses in a femtosecond (fs) time range. For example, the spectral phase coherent pulses can be in a range of about 5 fs to 100 fs. For example, a Ti:Sapphire laser oscillator capable of generating 20 fs full-width at half maximum (FWHM) spectral phase coherent pulses at 80 MHz, centered at 815 nm (corresponding to a bandwidth of about 75 nm or an energy span of 1100 $cm^{-1}$) can be employed for the purpose of the present invention.

The pulse controlling assembly (pulse shaper) 16 is configured and operable for tailoring the input spectral phase coherent driving pulse P to produce a unitary optical excitation pulse carrying the pump, Stokes and probe photons, and to provide phase and polarization conditions for desired frequencies (either in an open-loop configuration or in an adaptive manner) of the pulse to ensure interference between Raman levels excited in the medium by the unitary optical excitation pulse and to enable appropriate filtering of the radiation coming from the medium. The tailoring of the input spectral phase coherent driving pulses consists of assigning desired phase and polarization to wavelength components of the spectral phase coherent optical pulse (preferably only in a predetermined wavelength range, i.e., outside that where the CARS signal is most likely to occur) so as to ensure interference between the CARS signals of different levels. To this end, the assembly includes dispersive elements 22A and 22B; a programmable Spatial Light Modulator (SLM) 24 located at the Fourier plane defined by focusing assemblies 26A and 26B. Preferably, also provided in the assembly 16 is a blocking element 28.

The light directing optics includes mirrors 30A and 30B accommodated so as to, respectively, direct the input spectral phase coherent pulse P generated by the laser 14 to the pulse controlling assembly 16 (i.e., to the dispersive element 22A, and direct a pulse P' resulting from the processing in the assembly 16 (coming from the dispersive element 22B) to the sample. It should be understood that each of these single-mirror elements may be replaced by one or more beam splitter and/or a set of mirrors, or any other known light deflecting means. The light directing optics further includes a focusing assembly 32A for focusing the processed pulse P' onto the medium under investigation, and a lens assembly 32B accommodated for collecting the output CARS signal coming from the medium and directing it to the detector. For example, the focusing assembly 32A includes an objective lens arrangement having a 0.2 numerical aperture (NA). The collection lens assembly 32B preferably has a numerical aperture similar or larger than that of the lens 32A. It should be noted that the focusing assembly 32A can also serve as a collecting optics in a back-scattered mode.

The dispersive assemblies 22A and 22B may be thin ruled reflective gratings (e.g., with 1200 lines/mm). The focusing elements can be achromat lenses (e.g., with a focal length of 100 mm). Though the above embodiment uses ruled reflective gratings at the input and output of the pulse controller to spatially disperse and recombine the various frequency components of the pulses, it should be pointed out that any other suitable dispersive elements can be used, e.g., transmission gratings, prisms, or combinations thereof. Furthermore, the function of the focusing assemblies 26A and 26B in defining the system Fourier plane (focal plane) at which the SLM 24 is located, can be fulfilled by any other element having positive focusing power, e.g., a concave mirror.

The programmable SLM 24 may be a liquid crystal based SLM of the type described by A. M. Weiner in the article published in Rev. Sci. Inst., 2000, V.71, P. 1929. This SLM includes two SLM pixel arrays having 128 pixels at its Fourier plane. The spectral resolution, determined by the spot size at the Fourier plane, can be better than 0.5 nm (equivalent to about 8 $cm^{-1}$). The SLM acts as a polarization rotator to distinguish between the polarizations of probe and pump photons to thereby enabling filtering of the output signals coming from the medium, and as a phase shaper to assign a desired spectral phase shaping to the wavelengths components of the input pulse. The SLM assembly suitable to be used in the system of the present invention may, for example, be of the type described by T. Brixner et al. in the articles published in Opt. Lett., 2001, V. 26, P. 557 and Appl. Phys., 2002, V. B74, P. S133. Such a programmable liquid crystal SLM includes two SLM liquid crystal pixel arrays (dual cell SLM) whose preferential axes are at right angles to each other and are rotated by ±45° relative to the polarization of the input laser pulse (denoted as the x direction). Any difference in the applied retardance between the two arrays results in modification of the input pulse polarization. In this technique, the SLM can act as both a controlled spectral phase mask and as a controlled waveplate.

The blocking element 28 may for example be a plate arranged for blocking, at the Fourier plane, wavelengths shorter than a predetermined wavelength (e.g., 780 nm) in the range of a CARS signal, as they can spectrally overlap an output CARS signal. In the present example, the blocking element 28 is arranged between the SLM 24 and the output focusing element 26B. It should, however, be understood that the blocking element 28 can be arranged either upstream or downstream of the SLM 24. Furthermore, the function of the blocking element 28 can be fulfilled by any sharp-edge long-pass filter, e.g., a dielectric filter.

The filter assembly 18 includes a polarizer 18A and a simple spectral filter 18B. The filtered output of the filter assembly 18 is collected by the detector unit 20 which can include either a single-point detector such as a photomultiplier tube or a pixel array detector (e.g., CCD).

The phase controlling assembly 16 operates in the following manner. The dispersive element 22A operates to spatially separate the frequency components of the input spectral phase coherent pulse. The input focusing element 26A focuses each of these frequency components to its specific position at the focal plane, where the SLM 24 is located. The blocking element 28 blocks at the Fourier plane wavelengths shorter than the predetermined wavelength. The SLM 24 is operative as an updateable filter to provide a complex and carefully designed probe pulse to ensure interference between the contributions from several vibrational levels in the CARS signal, and to provide orthogonal polarizations for broadband pump and narrow band probe photons to enable filtering of the signal coming from the medium. The assembly is operable by the suitable control unit for separating between different frequency components of the input pulse, blocking the predetermined frequencies (higher frequencies, which can overlap the CARS signal); and assigning the desired phase and polarization to each frequency component of the remaining (unblocked) portion of the input pulse by using any desired spectral phase function. This will be described more specifically further below. The SLM output is focused onto the output grating 26B which recombines each of the separated processed frequency components into the pulse P'.

The CARS spectrometer system 10 may utilize an open loop control, in which the applied spectral phase function is derived theoretically for each experiment, or may utilize a closed feedback loop for determining the applied spectral phase function.

The measurable Raman energy range of the system 10 can, for example, be about 300 cm$^{-1}$-900 cm$^{-1}$, that is typical of carbon-halogen bond stretching. The lower limit of the measurable energy range is determined by the need to filter out the excitation pulse, while the upper limit is dictated by the excitation pulse bandwidth. Since the technique does not require electronic resonance with the driving input field, it can be implemented with any broadband optic source. The measurable Raman energy range of the system can be extended to the fingerprint region (900 cm$^{-1}$-1500 cm$^{-1}$) by using pulses of duration 10 fs-20 fs, available in state-of-the-art commercially available lasers [12].

Figure 3A:
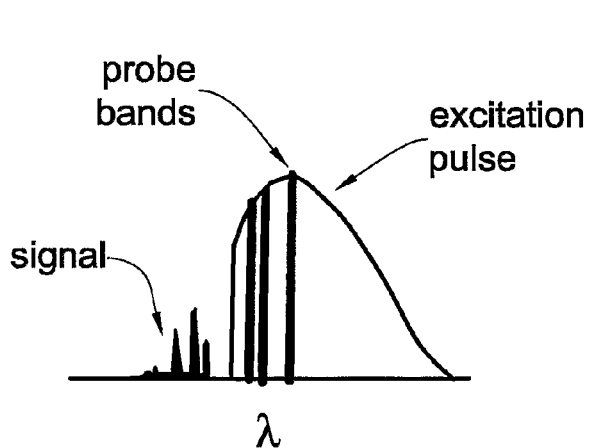
Figure 3B:
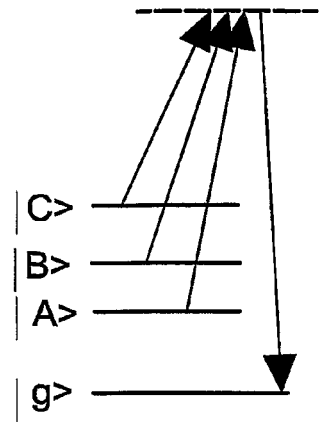

Reference is now made to FIGS. 3A and 3B. FIG. 3A shows a schematic description of the excitation pulse, blocked at its high frequency (short wavelength) end, the polarization shifted spectral bands serving as probe in the CARS process and the resulting signal. It should be noted that a predetermined spectral phase can be applied to both the polarization shifted bands and the unshifted broadband pump. FIG. 3B shows a schematic description of the interference in the CARS spectrum when several Raman bands are excited and probed by correspondingly chosen narrow spectrum probe bands. According to the present invention, the probe pulse is constructed to contain contributions from several narrow spectral bands with controllable intensities and phases (FIG. 3A).

As described in the inventors co-pending U.S. application Ser. No. 10/353,063, splitting off the broadband excitation pulse (input laser pulse) a single narrow spectral band around a frequency $\omega_{pr}$ for use as probe by shifting its polarization into the orthogonal axis, would result in that a CARS signal induced by this probe is composed of several spectral components, each associated with a particular vibrational frequency $\Omega''_R$, and centered at $\omega_{pr}+\Omega''_R$, respectively. The instantaneous nonresonant background is eliminated by introducing an internal phase structure to the probe spectral band, eliminating its temporal overlap with the broadband pump.

According to the present invention, several spectrally separated probe frequencies are provided, which frequencies include those defined by the expected vibrational levels selected so as to cause interference between n vibrational levels (at least some of the vibrational levels), namely $\omega_1+\Omega_1=\omega_i+\Omega_i$, wherein i=2, ..., n.

The provision of several spectrally separated probe frequencies leads to strong interference effects in the CARS spectrum (FIG. 3B). This interference pattern can be used in two ways to improve delectability in coherent Raman spectroscopy. When attempting to detect a given substance, coherent addition of the contributions from several vibrational levels can be performed, generating a total signal which is significantly larger than the linear sum of the separate contributions. When attempting to eliminate a resonant background it is possible to interfere destructively the contributions from several levels resulting in significant decrease of the background intensity.

When characterizing the CARS signal driven by an electric field whose complex spectral amplitude is $\in(\omega)$, for a singly resonant Raman transition through an intermediate level |i> at an energy of $\hbar\Omega_R$ and a bandwidth Γ we obtain [7]:

$$P_j^{(3)}(\omega) \propto \chi^r_{jklm} \int_0^\infty d\Omega \cdot \frac{\varepsilon_k(\omega-\Omega)}{(\Omega_R-\Omega)+i\Gamma} A_{lm}(\Omega) \quad (1)$$

wherein $A_{lm}(\Omega) \propto \int d\omega \in_1^*(\omega-\Omega)\in_m(\omega)$ is the second order polarization driving molecular vibrations, and jklm denote the electric field polarizations.

As indicated above (as resulted from the polarization control), the resonant CARS process is considered where the molecular vibration is excited by a broadband pulse polarized along the x-axis and probed by a pulse polarized along the y-axis. Now an expression for the CARS signal is derived under two conditions: the first is that there is no temporal overlap between the x-polarized pump and the y-polarized probe (i.e. the resonant $\chi_{jklm}$, term can be neglected and the nonresonant response vanishes), and the second is that $A_{yy}$ is negligible. In practice, the conditions of the former can be achieved by phase control of the probe component [6] and the latter by shifting only a small portion of the pulse energy or a narrow spectral band to the probe polarization.

In this case the nonlinear polarization driving the y-polarized CARS signal can be approximated as:

$$P_y^{(3)}(\omega) \propto \sum_n \chi_{yyxx}^n \int_0^\infty d\Omega \cdot \frac{\varepsilon_y(\omega - \Omega)}{(\Omega_R^n - \Omega) + i\Gamma^n} A_{xx}(\Omega) \quad (2)$$

The summation goes over all resonant Raman transitions through intermediate levels at energies $\hbar\Omega_R^n$ with bandwidths $\Gamma^n$ and relative strengths $\chi_{yyxx}^n$.

We now assume that the probe pulse is comprised of a number of narrow spectral bands of a width $\Delta$, each centered at a frequency $\omega_j$ and having an amplitude $|C_j|$ and an overall phase $\phi_j$, as well as an internal phase structure eliminating its temporal overlap with the broadband pump. For example, in the case of a phase flip at the band center (as shown in FIG. 7B and will be described more specifically further below), $\in(y)$ can be expressed as:

$$\varepsilon_y(\omega) = \sum_j |C_j| e^{i\phi_j} \left[ \begin{array}{c} \text{rect}\left(\frac{\omega - \omega_j - \Delta/4}{\Delta/2}\right) - \\ \text{rect}\left(\frac{\omega - \omega_j + \Delta/4}{\Delta/2}\right) \end{array} \right] \quad (3)$$

Assuming now that all linewidths $\Gamma^n$ and the probe bandwidth $\Delta$ are significantly smaller than the pulse bandwidth, $A_{xx}(\Omega)$ can be taken out of the integral of equation 2, which can then be approximated as a double sum over all resonant Raman levels and probe bands:

$$P_y^{(3)}(\omega) \approx \sum_{j,n} \chi_{eff}^n |C_j| e^{i\phi_j} \delta(\omega_j + \Omega_R^n - \omega) \quad (4)$$

wherein $\chi_{eff}^n = K_n \chi_{yyxx}^n A_{xx}(\Omega_R^n)$ and $K_n$ is an order unity coefficient evaluated from both the level linewidth and the probe bandwidth according to equations 2 and 3. In practice, the $\delta$ function of equation (4) has a width determined by the convolution of the Raman level linewidth and the bandwidth of each of the probe bands.

As can be seen in equation (4), there is symmetry between the vibrational levels and the narrow probe bands. Interference between contributions from several vibrational levels appears when the energy separation of the probe spectral bands equals the energy separation of the Raman levels, as shown schematically in FIG. 3B.

Turning back to FIG. 2, the inventors used this system to demonstrate utilization of the interference pattern in CARS spectroscopy of several simple molecules in the liquid phase. In the experimental system, a modelocked Ti:Sapphire laser was used emitting 20 femtosecond pulses at 80 MHz. The pulse controller (or pulse shaper) was used for both applying the desired phase and polarization [9] to each frequency component of the pulse, and to block the higher frequencies, overlapping the CARS signal [6, 10]. The sample was illuminated by pulses with a total bandwidth of 75 nm, equivalent to a span of about 1100 cm$^{-1}$ and energy of about 0.1 nJ. After passage through the sample, the excitation pulse was filtered out, and the CARS signal polarized parallel to the probe was measured. This system is suitable for CARS spectroscopy in the range of about 300 cm$^{-1}$-900 cm$^{-1}$, typical of carbon-halogen bond stretching. The lower limit stems from the technical requirement to filter out the excitation pulse, and the upper limit is due to the total bandwidth of the excitation pulse. The spectral resolution is about 0.5 nm, corresponding to about 8 cm$^{-1}$.

Figure 4A:
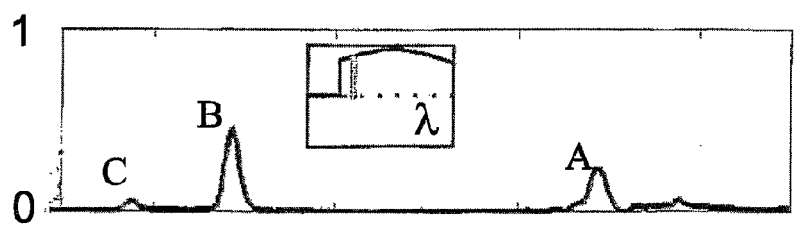
Figure 4B:
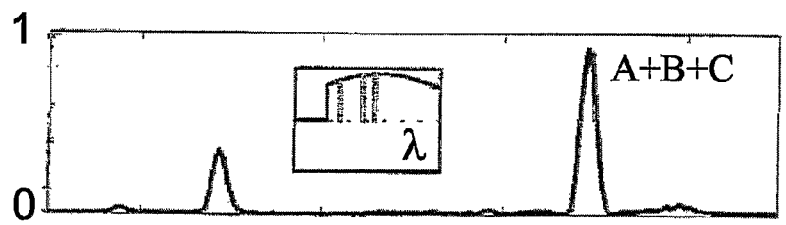
Figure 4C:
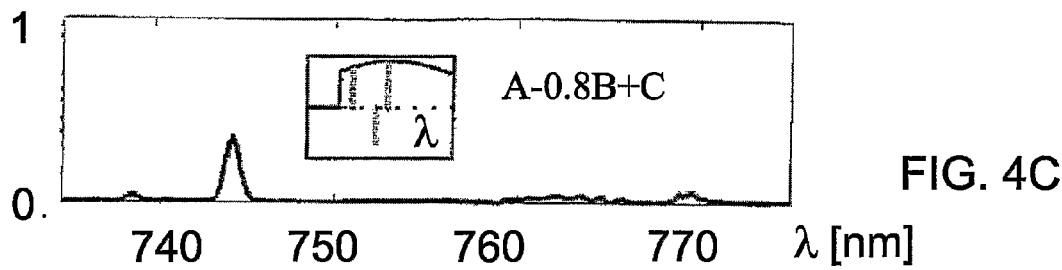

Referring to FIGS. 4A-4C, there are shown experimental results. Here, the insets denote the spectral masks (spectral functions) used, where the excitation spectrum is shown in black, and the polarization shifted probe bands are shown in gray. In practice, each of these probe bands has a width of 1.2 nm and a phase flip at its center, as defined in equation 3. The background due to birefringence of the objective lens has been subtracted from all the following spectra.

CARS spectroscopy was performed for 1,2-dichloroethane, having three Raman levels in the measurable energy range. A CARS spectrum obtained using a single narrow-band probe at $\omega_A$, corresponding to $\lambda=782$ nm, and following the method of Ref. [6] is shown in FIG. 4A. Three peaks A, B and C are shown corresponding to the Raman levels at respectively $\Omega_A=298$ cm$^{-1}$, $\Omega_B=652$ cm$^{-1}$, and $\Omega_C=750$ cm$^{-1}$. The observed intensity ratios, reflecting $\chi_{eff}$ for each level are 4.5:9:1, respectively.

Considering first the case when 1,2-dichloroethane is to be detected more efficiently, two more spectral bands, $\omega_B$ and $\omega_C$, are shifted (from the broadband pump spectrum) to the probe polarization, so that the interference condition is satisfied:

$$\omega_A + \Omega_A = \omega_B + \Omega_B = \omega_C + \Omega_C$$

In this case the CARS signals from all three levels spectrally overlap at the spectral location of peak A of FIG. 4A.

As shown in FIG. 4B, when all probe bands are in phase, constructive interference of all three contributions is achieved. This is the CARS spectrum obtained using a pulse with three probe bands (at 782 nm, 804 nm, 811 nm) all in phase and fully y-polarized, designed to induce constructive interference between the contributions of the three levels to the peak at 764 nm. The observed ratio of the total peak A to peak B is 2.6, significantly higher than the 1.6 ratio expected from an incoherent summation. It is still lower than the theoretical value for a coherent sum, 4.2, only due to the pixellization of the pulse shaper, which does not allow to completely overlap the three contributions spectrally. The constructive interference significantly increases the delectability of weak Raman levels due to heterodyning with stronger ones. Moreover, the detection process does not require measurement of the entire CARS spectrum. It should be noted that the peaks B (at 739 nm) and C (at 744 nm) contain only a contribution from the probe band at 782 nm ($\omega_A$), and are therefore almost unchanged relative to that of FIG. 4A. The slight decrease in their intensity is due to the somewhat smaller peak intensity of the pump pulse due to the additional probe bands.

FIG. 4C shows the CARS spectrum obtained using a pulse with three probe bands designed to induce destructive interference at 764 nm between the contributions of the three levels (in this case the overall phase of the probe band at 804 nm was inverted, and the SLM was set to act as a 0.35$\lambda$ plate, so less energy is transferred to the y-polarization). This experiment relates to the case where 1,2-dichloroethane is a solvent in which a low-concentration solute having a Raman level overlapping one of the solvent levels is to be detected. In this case, the phase of the probe band $\omega_B$ was inverted and its intensity was reduced by 20% by shifting less energy to the orthogonal polarization. As shown, the peak at 764 nm is completely eliminated due to destructive interference of the three levels. It should be noted that other peaks in the CARS spectrum, where interference effects are not present, remain the same as in FIG. 4B. This destructive interference is highly specific to the level structure of 1,2-dichloroethane. Any substance with a different line strength ratio of the three probed levels would thus generate a finite CARS signal at this spectral location.

Thus the pulse controlling consists, in this case, of splitting the pulse into a pump component and multiple probe components, wherein the pump and probe have substantially orthogonal polarizations, and of assigning a desired phase to the wavelength components of the spectral phase coherent optical pulse. The assigning of the desired phase consists of applying to the input pulse a desired spectral phase function. The latter is achieved by applying an overall desired constant phase to each of the probe spectral components as well as several phase gates spectrally located within the spectral components of the probe components, and having a bandwidth narrower than that of each probe component and substantially narrower than the bandwidth of the unitary excitation pulse to be produced.

FIGS. 5A and 5B exemplify the effect of a single $\pi$ phase-shifted gate 110 introduced at a y-polarization shifted band 111, serving as a probe. FIG. 5A shows the spectral intensity of a phase and polarization shaped excitation pulse. The probe is split into two spectrally distinct longer probe pulses with opposite phase. Due to the broad nonresonant spectral response, the nonresonant background from these two probe pulses interferes destructively. Since the $A_{xx}(\Omega)$ component of the amplitude is a very smooth function, these two probe pulses are almost equal in magnitude. As a result, the nonresonant background component of the CARS signal can be reduced by orders of magnitude.

This reduction can be alternatively viewed in time domain. FIG. 5B shows a schematic drawing of the electric field envelope versus time in both the x-polarization (curve 121) and the y-polarization (curve 122) for both phase and polarization shaped pulse. For convenience, the x-polarization field has been reduced by about two orders of magnitude. As can be appreciated, the $\pi$ phase gate modifies the temporal shape of the y-polarized probe so that the electric field envelope crosses zero at the peak of the x-polarized driving field.

Due to the instantaneous nonresonant response, the nonresonant background is almost completely suppressed. The resonant signal response is different. It should be noted that the $\pi$ phase gate compensates for the sign inversion of the denominator in equation (2), leading to an increased resonant signal over a narrow spectral band shifted by the Raman level energy from the $\pi$ phase gate location.

Exact knowledge of the Raman level structure of the probed medium is often missing. This does not, however, limit the applicability of the technique of the present invention due to the availability of adaptive techniques [11]. In an adaptive search, a pulse shape is searched which maximizes some goal function. The measurement result is fed back into the control unit which, using a search algorithm, decides on the next measurement.

Reference is made to FIGS. 6A-6C exemplifying an adaptive optimization of the signal at 765 nm from 1,2-dichloropropane. In FIG. 6A, the signal at 765 nm is shown during five iterations of the optimization procedure. The signal increases by about a factor of three from the peak of the first iteration (using a single probe band) to that of the fifth iteration (using five probe bands, all in phase with each other). FIG. 6B shows the measured CARS spectrum at the end of the first iteration. FIG. 6C shows the measured CARS spectrum at the end of the fifth iteration.

In the present example, the goal function is selected so as to maximize the total signal at 765 nm from a sample of 1,2-dichloropropane. Following the heuristics of a coherent addition of a number of separate bands, a greedy optimization algorithm is selected. In each of the iterations, a single new probe band is added, keeping fixed all probe bands from previous iterations. The new spectral location is chosen to maximize the goal function, as long as it is spectrally separated from previous locations. As shown in FIG. 6C, the pulse contains five separate probe bands, corresponding to vibrational energies of 285 cm$^{-1}$, 352 cm$^{-1}$, 419 cm$^{-1}$, 623 cm$^{-1}$, and 741 cm$^{-1}$ (all ±8 cm$^{-1}$), which indeed correspond to the five strongest Raman levels of 1,2-dichloropropane in the measured energy region.

The experiment shows how coherent analysis of the Raman spectrum can be performed using shaped ultrashort pulses. The shaped pulse acts in an analogous manner to a matched filter in frequency domain, by use of which information on the correlation of the measured Raman spectrum with a given spectrum can be obtained. In particular, this method enables rejection not only of the nonresonant background, but also of the resonant background, due to an overlapping Raman level of the probed substance and the surrounding medium. Using current day laser systems this technique can be used to perform vibrational spectroscopy in the entire fingerprint spectral region [12] with a resolution of the order of typical Raman linewidths. The method of the present invention is particularly attractive for the detection of trace amounts of a substance in the presence of strong resonant Raman background. The combination of adaptive pulse shaping with CARS spectroscopy has been recently suggested as a means to detect airborne contaminants such as bacterial spores [13]. It can also be applied to significantly improve the signal to background ratio in Raman optical biopsy, where small changes in ratios of chemical constituents within a cell are probed by changes in the relative strengths of Raman lines [14]. The concept of utilizing the coherence properties of the Raman signal provides a significant impact on CARS microspectroscopy as well as on other coherent nonlinear spectroscopy applications.

The present invention also provides a method suitable for performing single-pulse two-dimensional Raman spectroscopy using phase-and-polarization coherent control to measure either the anharmonicity of a single vibrational mode or the coupling between two excited states, and thus provide structural information about the probed medium (in analogy with NMR technique). According to this technique, one of the two time scales is introduced by applying periodic phase modulation of the x-polarized component of the excitation pulse, i.e., applying a periodic spectral phase function to assign a desired phase to the wavelength components of the input pulse (e.g., using a sinusoidal function). As an example, the intensity and phase modulation of this pump is depicted in FIG. 7A. The second time scale is introduced by spectrally dispersing the signal from a shaped, narrow-bandy-polarized probe. In order to avoid temporal overlap with the shaped pump pulse, this y-polarized probe can contain an internal phase structure as discussed above. Two such shapes are shown in FIGS. 7B-7C. The shape of FIG. 7B is similar to that shown in FIGS. 5A-5B, where there is a $\pi$phase flip at the center of the probe band. The other shape, where a $\pi$-phase flip of a band corresponding to half of the bandwidth of the probe band centered with the probe band, is shown in FIG. 7C. The normalized temporal intensities of the modulated pump pulse and the two shaped probe pulses are shown in FIG. 7D. The probe-free time window can be seen to be significantly longer with the probe shape of FIG. 7C, and can be further elongated by more complex phase shapes. This multidimensional spectroscopy scheme is a significant simplification of typical 2D spectroscopy setups, which typically require interferometric stability of a number of excitation beams.

Those skilled in the art will readily appreciate that various modifications and changes can be applied to the embodiment of the present invention as hereinbefore exemplified without departing from its scope defined in and by the appended claims.

The invention claimed is:

1. A method for producing exciting radiation to be used in producing an output coherent anti-stokes Raman scattering (CARS) signal of a medium, the method comprising: tailoring an input spectral phase coherent optical pulse carrying a pump photon, a Stokes photon and a probe photon, said tailoring comprising adjusting spectral phase and polarization of wavelength components of the spectral phase coherent optical pulse to produce a unitary optical exciting pulse that carries the pump photon, the Stokes photon and multiple probe photons and is capable of inducing a CARS signal, which results from an interference between contributions from at least two vibrational levels.

2. The method of claim 1, wherein the multiple probe photons include those defined by the expected vibrational levels and selected so as to cause the interference between n vibrational levels, such that $\omega_1+\Omega_1=\omega_i+\Omega_i$, i=2, ..., n, wherein $\omega$ is the probe frequency and $\Omega$ is the frequency of the respective vibrational level.

3. The method of claim 1, wherein said tailoring resulting in that a CARS spectrum is concentrated in a single spectral component, thereby significantly simplifying filtering of a signal coming from the medium to extract the CARS signal therefrom.

4. The method of claim 1, wherein the spectral phase is adjusted to obtain either constructive or destructive interference for the at least two of the vibrational levels.

5. The method of claim 1, wherein the tailoring of the spectral phase coherent optical pulse includes blocking wavelengths shorter than a predetermined wavelength in the input pulse.

6. The method of claim 5, wherein said predetermined wavelength is defined by a spectral bandwidth in which the output CARS signal is likely to occur.

7. The method of claim 1, wherein the tailoring comprising assigning a desired phase and polarization to each of the wavelength components of the input spectral phase coherent optical pulse, and providing orthogonal polarizations for the probe and pump photons, respectively.

8. The method of claim 7, comprising rotating the polarization of the probe components of the input pulse to be orthogonal to that of the pump photons; assigning a desired phase to each of the probe components, comprising both an internal phase structure and an overall phase; and assigning the desired phase to the pump components.

9. The method of claim 7, wherein the desired phase and polarization is assigned by modulating the spectral phase of two orthogonal polarization components of the input spectral phase coherent optical pulse using a desired spectral phase function.

10. The method of claim 9, wherein the spectral phase function defines a set of polarization gates of variable polarization rotations, in accordance with the probe photon wavelengths corresponding to the vibrational levels to be excited, and providing each of the polarization gates with both an overall constant phase and a desirable internal phase structure, so as to ensure interference between at least two of the vibrational levels.

11. The method of claim 10, wherein the internal phase structure consists of a number of phase gates spectrally located within the spectral components of the probe components, and having a bandwidth narrower than that of each probe component and substantially narrower than the bandwidth of the unitary excitation pulse to be produced.

12. The method of claim 10, wherein the internal phase structure consists of a number of T-phase gates of variable bandwidths.

13. The method of claim 11, wherein the tailored excitation pulse provides all the probe gates to be in phase, thus inducing coherent addition of the contributions from the several vibrational levels, to thereby generate the total excited signal which is significantly larger than a linear sum of the separate contributions.

14. The method of claim 11, wherein the tailoring of the excitation pulse adjusts the probe gates phases so as to cause the destructive interference between the contributions from the several vibrational levels, thus significantly reducing a resonant background in the excited CARS signal.

15. The method of claim 9, wherein the spectral phase function applied to the pump components is a periodic function, the method thereby enabling measuring anharmonicity or coupling between two excited states and thus providing structural information about the medium.

16. The method of claim 11, comprising introducing one of two time scales by applying the periodic spectral phase function to one polarization component of the exciting pulse, and introducing the second time scale by spectrally dispersing the signal from the shaped narrow-band probe photon of the orthogonal polarization.

17. A method for producing exciting radiation to be used in producing an output coherent anti-stokes Raman scattering (CARS) signal of a medium, the method comprising: tailoring an input spectral phase coherent optical pulse carrying a pump photon, a Stokes photon and a probe photon, said tailoring comprising adjusting spectral phase and polarization of wavelength components of the spectral phase coherent optical pulse to produce a unitary optical exciting pulse that carries the pump photon, the Stokes photon and multiple probe photons and is capable of inducing a CARS signal, which results from an interference between contributions from at least two vibrational levels, a CARS spectrum therefore being concentrated in a single spectral component, thereby significantly simplifying filtering of a signal coming from the medium to extract the CARS signal therefrom.

18. A method for producing an output coherent anti-stokes Raman scattering (CARS) signal of a medium, the method comprising:
(i) generating an input spectral phase coherent optical pulse carrying a pump photon, a Stokes photon and a probe photon;
(ii) applying a predetermined tailoring to the input pulse, the tailoring comprising adjusting spectral phase and polarization of wavelength components of the input pulse to produce a unitary optical exciting pulse that carries the pump photon, the Stokes photon and multiple probe photons and is capable of inducing interference between contributions from vibrational levels in the CARS signal excited in the medium by said exciting pulse, said multiple photons having the same polarization which is orthogonal to that of the pump photons;
(iii) passing radiation coming from the medium through a polarizer to thereby separate the excited CARS signal from a background.

19. A system for use in measuring an output coherent anti-stokes Raman scattering (CARS) signal of a medium, the system comprising a pulse shaper assembly configured and operable to apply tailoring to an input coherent optical pulse, said tailoring comprising adjusting spectral phase and polarization of wavelength components of the spectral phase coherent optical pulse to produce an exciting pulse that carries desired wavelength components and is capable of, when interacting with the medium, inducing interference between contributions from several vibrational levels in the CARS signal excited in the medium.

20. The system of claim 19, wherein said phase shaper operates to provide the multiple probe photons including those defined by the expected vibrational levels and selected so as to cause the interference between n vibrational levels, such that $\omega_1+\Omega_1=\omega_i+\Omega_i$, i=2, ..., n, wherein $\omega$ is the probe frequency and $\Omega$ is the frequency of the respective vibrational level.

21. The system of claim 19, wherein said phase shaper operates to adjust the phase of the wavelength components so as to obtain either constructive or destructive interference for at least some of the vibrational levels.

22. The system of claim 19, wherein the phase shaper comprises a radiation blocking assembly configured and operable to block wavelengths shorter than a predetermined wavelength in the input pulse.

23. The system of claim 22, wherein said predetermined wavelength is defined by a spectral bandwidth in which the output CARS signal is likely to occur.

24. The system of claim 19, wherein the phase shaper is configured and operable to assign a desired phase and polarization to each of the wavelength components of the input spectral phase coherent optical pulse, and provide orthogonal polarizations for the probe and pump photons, respectively.

25. The system of claim 24, wherein the phase shaper is configured and operable to modulate a spectral phase of the input spectral phase coherent optical pulse using a desired spectral phase function.

26. The system of claim 25, wherein the spectral phase function defines a set of polarization gates of variable polarization rotations, and providing each of the polarization gates with both an overall constant phase and a desirable internal phase structure, in accordance with the probe photon wavelengths corresponding to the vibrational levels to be excited.

27. The system of claim 26, wherein the internal phase structure consists of a number of phase gates spectrally located within the spectral components of the probe components, and having a bandwidth narrower than that of each probe component and substantially narrower than the bandwidth of the unitary excitation pulse to be produced.

28. The system of claim 26, wherein the internal phase structure consists of a number of $\pi$-phase gates of variable bandwidths.

29. The system of claim 25, wherein the desired spectral phase function of the pump components is a periodic function, the system thereby enabling measuring coupling between two excited states and thus providing structural information about the medium, based on a first time scale obtained by applying the periodic spectral phase function to one polarization component of the exciting pulse, and a second time scale obtained by spectrally dispersing the signal from the shaped narrow-band probe photon of the orthogonal polarization.

30. The system of claim 19, wherein the phase shaper is configured and operable to provide all the probe photons to be in phase, thus inducing coherent addition of the contributions from the several vibrational levels, to thereby generate the total excited signal which is significantly larger than a linear sum of the separate contributions.

31. The system of claim 19, wherein the phase shaper is configured and operable to adjust the probe photon phase so as to cause the destructive interference between the contributions from the several levels, thus significantly reducing a resonant background in the excited CARS signal.

32. The system of claim 19, wherein the phase shaper includes an input dispersive element for spatially separating between the wavelength components in the input pulse; a Spatial Light Modulator (SLM) operable to apply spectral phase shaping and polarization rotation to selected components from said wavelength components; and an output dispersive element for recombining at least some of the wavelength components into the output exciting pulse.

33. The system of claim 32, wherein the phase shaper includes a spectral filter operable to block a desired wavelength range in the input pulse to prevent radiation of this wavelength range from reaching the medium.

34. The system of claim 32, wherein the SLM is operable to apply to radiation passing therethrough a predetermined spectral phase function so as to provide in the exciting pulse the pump, Stokes and probe photons, such that the probe photons include those defined by the expected vibrational levels selected so as to cause interference between at least some of the vibrational levels.

35. The system of claim 34, wherein the SLM operates to provide orthogonal polarizations for the pump and probe photons, respectively.

36. The system of claim 19, comprising a filter assembly for filtering a signal coming from the medium to extract the CARS signal therefrom.

37. The system of claim 36, wherein said filter assembly comprising a polarizer, and a spectral filter that is configured to separate from the signal coming from the medium a single spectral component to which the CARS spectrum is concentrated as a result of said tailoring.

38. A system for use in measuring an output coherent anti-stokes Raman scattering (CARS) signal of a medium, the system comprising:
a single laser operable to generate at least one input spectral phase coherent optical pulse carrying a pump photon, a Stokes photon and a probe photon; and
a pulse shaper assembly configured and operable to tailor the input pulse, said tailoring comprising adjusting spectral phase and polarization of wavelength components of the input pulse to produce an exciting pulse that carries desired wavelength components including the pump photon, the Stokes photon and multiple probe photons and is capable of, when interacting with the medium, inducing interference between contributions from several vibrational levels in the CARS signal excited in the medium;
a polarizer assembly for accommodating in an optical path of radiation coming from the medium to filter this radiation to extract the CARS signal from a background radiation.

39. A system for use in measuring an output coherent anti-stokes Raman scattering (CARS) signal of a medium, the system comprising:
a pulse shaper assembly configured and operable to apply tailoring to an input coherent optical pulse, said tailoring comprising adjusting spectral phase and polarization of wavelength components of the spectral phase coherent optical pulse to produce an exciting pulse that carries desired wavelength components and is capable of, when interacting with the medium, inducing interference between contributions from several vibrational levels in the CARS signal excited in the medium, a spectrum of the CARS signal being therefore concentrated to a single spectral component;

a filter assembly for accommodating in a path of radiation coming from the medium, the filter assembly comprising a polarizer, and a spectral filter configured for separating the single spectral component from the radiation coming from the medium.

* * * * *

UNITED STATES PATENT AND TRADEMARK OFFICE
CERTIFICATE OF CORRECTION

| | | |
|---|---|---|
| PATENT NO. | : 7,826,051 B2 | |
| APPLICATION NO. | : 11/597190 | |
| DATED | : November 2, 2010 | |
| INVENTOR(S) | : Yaron Silberberg, Nirit Dudovich and Dan Oron | |

It is certified that error appears in the above-identified patent and that said Letters Patent is hereby corrected as shown below:

On claim 12, column 18, line 8, please delete:

"T-phase" and replace with: -- $\pi$-phase --

Signed and Sealed this
Twenty-second Day of March, 2011

David J. Kappos
*Director of the United States Patent and Trademark Office*